(12) United States Patent
Carballada et al.

(10) Patent No.: US 6,585,965 B1
(45) Date of Patent: Jul. 1, 2003

(54) HAIR CARE COMPOSITIONS COMPRISING POLYALKYLENE GLYCOL STYLING AGENTS

(75) Inventors: Jose Antonio Carballada, Cincinnati, OH (US); Dennis Eugene Kuhlman, Middletown, OH (US); Michael John Schneider, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/631,317

(22) Filed: Aug. 3, 2000

(51) Int. Cl.[7] .............................. A61K 7/06; A61K 7/07; A61K 7/075; A61K 7/08; A61K 7/11

(52) U.S. Cl. ..................... 424/70.1; 424/47; 424/486; 424/70.12; 424/70.15; 424/DIG. 1; 424/DIG. 2

(58) Field of Search ..................... 424/70.1, 47, 486, 424/70.12, 70.15, DIG. 1, DIG. 2

(56) References Cited

U.S. PATENT DOCUMENTS

| | | | |
|---|---|---|---|
| 3,215,603 A | 11/1965 | Gross et al. | 167/87 |
| 3,427,382 A | 2/1969 | Haefele et al. | 424/71 |
| 3,876,760 A | 4/1975 | Nersesian et al. | 424/70 |
| 3,959,463 A | 5/1976 | Nersesian et al. | 424/70 |
| 4,001,392 A | 1/1977 | Curry et al. | 424/47 |
| 4,425,329 A * | 1/1984 | Tsutsumi et al. | 424/70 |
| 4,902,499 A | 2/1990 | Bolich, Jr. et al. | 424/70 |
| 5,211,941 A | 5/1993 | Komori et al. | 424/70 |
| 5,216,033 A * | 6/1993 | Pereira et al. | 514/844 |
| 5,275,761 A | 1/1994 | Bergmann | 252/551 |
| 5,342,611 A | 8/1994 | Komori et al. | 424/70 |
| 5,358,667 A | 10/1994 | Bergmann | 252/547 |
| 5,362,484 A | 11/1994 | Wood et al. | 424/70 |
| 5,456,863 A | 10/1995 | Bergmann | 252/547 |
| 5,660,190 A | 8/1997 | Tricaud et al. | 132/208 |
| 5,733,536 A | 3/1998 | Hill et al. | 424/70.12 |
| 5,750,122 A | 5/1998 | Evans et al. | 424/401 |
| 5,837,661 A | 11/1998 | Evans et al. | 510/122 |
| 5,874,092 A | 2/1999 | Roulier et al. | 424/401 |
| 6,214,319 B1 | 4/2001 | Franzke et al. | |

FOREIGN PATENT DOCUMENTS

| | | | |
|---|---|---|---|
| EP | 268 982 | 11/1987 | A61K/7/06 |
| EP | 313 307 | 10/1988 | A61K/7/11 |
| EP | 566 049 | 4/1993 | A61K/7/08 |
| EP | 682 935 | 5/1995 | A61K/7/06 |
| EP | 240 350 | 6/1995 | A61K/7/11 |
| EP | 820 758 | 7/1997 | A61K/7/06 |
| EP | 916 690 | 11/1998 | C08J/3/03 |
| JP | 2634858 | 12/1989 | A61K/9/12 |
| JP | 04290810 | 10/1992 | A61K/7/00 |
| JP | 10167935 | 12/1996 | A61K/7/06 |
| JP | 10-007534 | 1/1998 | A61K/7/06 |
| JP | 2750807 | 2/1998 | A61K/7/06 |
| JP | 10167948 | 6/1998 | A61K/7/48 |
| JP | 00/204025 A2 | 7/2000 | |
| WO | WO 95/09599 | 4/1995 | A61K/7/06 |
| WO | WO 97/30681 | 8/1997 | A61K/7/06 |
| WO | WO 97/30682 | 8/1997 | A61K/7/06 |
| WO | WO 98/38969 | 9/1998 | A61K/7/00 |
| WO | WO-00/40212 A1 | 7/2000 | |
| WO | WO-00/67709 A2 | 11/2000 | |

* cited by examiner

Primary Examiner—Frederick Krass
Assistant Examiner—Clinton Ostrup
(74) Attorney, Agent, or Firm—Linda M. Sivik; Brian M. Bolam; Tara M. Rosnell

(57) ABSTRACT

Hair care compositions comprise a water-soluble polyalkylene glycol having a number average molecular weight of from about 200 to about 900 and from about 4 to about 18 repeating alkylene oxide radicals, wherein each of the repeating alkylene oxide radicals has from 2 to 6 carbon atoms; a film forming polymer is soluble in the polyalkylene glycol, wherein the weight ratio of the polyalkylene glycol to the film forming polymer ranges from about 5:1 to about 50:1; and a liquid carrier. The hair care compositions optionally further comprise a non-volatile silicone with a molecular weight greater than about 40,000 daltons.

19 Claims, No Drawings

HAIR CARE COMPOSITIONS COMPRISING POLYALKYLENE GLYCOL STYLING AGENTS

FIELD OF THE INVENTION

The present invention is directed to hair care compositions. In particular, the present invention is directed to hair care compositions which include polyalkylene glycol styling agents and which exhibit an advantageous combination of improved hair restyling performance and improved hair look and feel without reapplication of the composition and/or application of additional hair care aids.

BACKGROUND OF THE INVENTION

Hair styling compositions are well known and are commercially available in a variety of forms including mousses, gels, lotions, pumps, or hair sprays. Many of these products contain various hair styling agents to provide temporary hair styling benefits such as body, hold, luster, improved hair feel, and good style retention.

One method of providing temporary hair styling benefits from a styling product involves the use of a hair gel. Many hair gel products have been formulated such that the hair gel composition can be applied to wet or damp hair before styling or "setting" the hair. Typically, the hair gel compositions are aqueous formulations which contain water-soluble styling agents that provide adhesive properties to the hair while the hair is wet and being styled. These styling agents, however, can form hard breakable films on the hair as the styling process nears completion, and this can result in an unacceptable hair style or in a hair style that cannot be restyled unless additional water and/or supplemental styling products are added to the hair. Moreover, the use of aqueous hair gel compositions which contain water-soluble styling agents can leave the hair feeling unduly sticky and stiff.

Various other aqueous hair gel compositions have been employed in attempts to improve hair styling performance and hair feel. Oftentimes, however, these hair gel compositions are applied to wet or damp hair to achieve the desired hair conditioning benefits and generally require reapplication of the composition or application of another styling product to maintain or modify the original hairstyle.

A recent method of making a hair styling composition that can be applied to wet and/or dry hair during the styling process is described in JP 8-346608, published Jun. 23, 1998. The hair styling compositions disclosed in this publication contain polyalkylene glyceryl ether styling agents to provide for sustained hair styling performance and aesthetics such as luster to the hair. These polyalkylene glyceryl ether styling agents typically do not readily penetrate into the hair and can remain on the hair fibers to provide hair styling benefits. The polyalkylene glyceryl ether-containing compositions disclosed in this particular publication, however, tend to provide minimal or no hold to the hair, and this can result in poor style achievement and poor style retention performance.

Another hair styling composition that can be applied during the styling process is described in WO 98/38969, published Sep. 11, 1998. The compositions disclosed in this publication use certain styling agents which deliver hair style performance to dry hair, and provide for the dry hair to be restyled without having to reapply the composition and without requiring the use of another styling product. The styling agents described in this reference include anionic, cationic, amphoteric, and nonionic styling polymers, preferably sulfonated anionic styling polymers which have an average molecular weight of from about 500 to about 5,000,000. These styling agents, however, have exceptional cohesive strength which provides for the hair fibers to be firmly held together, and this can cause the dry hair to feel coarse and to be difficult to comb, style and restyle.

Recently, it has become known to utilize hair styling compositions containing polyalkylene glycol styling agents. These hair styling compositions are described in U.S. application Ser. No. 09/305,502 and are advantageous in that they provide for improved dry hair restyling performance without the need to reapply the composition and/or apply additional styling aids.

In order to provide such compositions with further improved performance, it would be advantageous to improve the styling strength delivered by the polyalkylene glycol styling agents, without having to increase to level of the polyalkylene glycol styling agents in the compositions.

SUMMARY OF THE INVENTION

It is therefore an object of the present invention to provide improved hair care compositions. It is a more specific object of the invention to provide hair care compositions which provide desirable wet and/or dry hair restyling performance. It is a further object of the invention to provide such compositions which also provide good hair look and feel. It is yet another object of the present invention to provide compositions which provide desirable wet and/or dry hair restyling performance and good hair look and feel for extended periods of time without the need to reapply the composition or apply any other styling aids. It is a further object of the present invention to provide leave-on hair styling compositions which do not feel unduly sticky or stiff after the composition has been applied and allowed to dry on the hair.

These and additional objects and advantages are provided by the present invention. In a first embodiment, the present invention is directed to hair care compositions which comprise (a) a water-soluble polyalkylene glycol having a number average molecular weight of from about 200 to about 900 and from about 4 to about 18 repeating alkylene oxide radicals, wherein each of the repeating alkylene oxide radicals has from 2 to 6 carbon atoms; (b) a film forming polymer, wherein the film forming polymer is soluble in the polyalkylene glycol and wherein the weight ratio of the polyalkylene glycol to the film forming polymer ranges from about 5:1 to about 50:1; and (c) a liquid carrier.

Another embodiment of the present invention is directed to hair care compositions which comprise (a) from about 5% to about 20% by weight of a water-soluble polyalkylene glycol having a number average molecular weight of from about 200 to about 900 and from about 4 to about 18 repeating alkylene oxide radicals, wherein each of the repeating alkylene oxide radicals has from 2 to 6 carbon atoms; (b) a film forming polymer, wherein the film forming polymer is soluble in the polyalkylene glycol and wherein the weight ratio of the polyalkylene glycol to the film forming polymer ranges from about 10:1 to about 40:1; and (c) a liquid carrier.

The present invention is also directed to hair care compositions which comprise (a) from about 5% to about 12%, by weight, of a water-soluble polyalkylene glycol having a number average molecular weight of from about 200 to about 900 and from about 4 to about 18 repeating alkylene oxide radicals, wherein each of the repeating alkylene oxide radicals has from 2 to 6 carbon atoms; (b) from about 0.25% to about 1.5%, by weight, of a film forming polymer, wherein the film forming polymer is soluble in the polyalkylene glycol and wherein the weight ratio of the polyalkylene glycol to the film forming polymer ranges from about 10:1 to about 40:1; and (c) from about 85% to about 95%, by weight, of a liquid carrier.

Yet another embodiment of the present invention is directed to hair care hair care compositions which comprise (a) from about 5% to about 12%, by weight, of a water-soluble polyalkylene glycol having a number average molecular weight of from about 200 to about 900 and from about 4 to about 18 repeating alkylene oxide radicals, wherein each of the repeating alkylene oxide radicals has from 2 to 6 carbon atoms; (b) from about 0.25% to about 1.5%, by weight, of a film forming polymer, wherein the film forming polymer is soluble in the polyalkylene glycol and wherein the weight ratio of the polyalkylene glycol to the film forming polymer ranges from about 5:1 to about 50:1; (c) from about 85% to about 95%, by weight, of a liquid carrier; and (d) from about 1% to about 5%, by weight, of a non-volatile silicone with a molecular weight greater than about 40,000 daltons.

The invention is also directed to methods for styling hair by applying an effective amount of such compositions to hair.

The hair care compositions of the present invention provide improved wet and/or dry hair restyling performance, such as 1) hair styling and restyling without reapplication of the compositions, or application of water and/or an additional styling aid, 2) hair restyling for several days by simply combing or brushing, and/or 3) desirable styling aesthetics including frizz and volume control, superior hold, and superior hair look and feel.

These and additional objects and advantages will be more readily apparent in view of the following detailed description.

DETAILED DESCRIPTION

The hair care compositions of the present invention comprise polyalkylene glycols which are deposited on the hair. While not intending to be limited by theory, it is believed that the compositions form reformable welds on the hair fibers. As will be understood hereafter, the most preferred embodiments of the present invention relate to compositions intended as leave-on hair styling products.

The term "leave-on" as used herein refers to compositions that contain ingredients that are intended to be deposited and left on the hair for extended periods (e.g., several hours or days) until the ingredients are subsequently removed by water and/or shampooing the hair.

The term "reformable weld" as used herein refers to residues which are left on dry hair and which contain materials that are liquid or semisolid at ambient conditions, and that can remain as a liquid or semisolid after the compositions described herein have been applied and allowed to dry on the hair.

The term "ambient conditions" as used herein refers to surrounding conditions at about one atmosphere of pressure, at about 50% relative humidity, and at about 25° C.

All percentages, parts and ratios are by weight of the total composition, unless otherwise specified.

In one embodiment, the polyalkylene glycol styling agent is in a continuous aqueous phase, in which an immiscible nonaqueous phase is optionally dispersed. One skilled in the art will appreciate however that the components which form the inventive compositions may be combined in a variety of forms and methods.

Styling Agent

The hair care compositions of the present invention comprise a water-soluble liquid or semisolid hair styling agent suitable for being left on hair as a liquid or semisolid after the composition has been applied and allowed to dry on the hair. It has been found that low molecular weight polyalkylene glycol liquid or semisolid styling agents can be delivered to the hair as a fluid film to be left on the hair which can be characterized as reformable welds that provide hair restyling performance. In particular, the reformable welds allow the hair fibers to be separated by forces such as wind, and then re-adhered using styling techniques such as combing, brushing, or running one's fingers through the hair. This separation/re-adherence property provided by the styling agents defined herein results in improved wet and/or dry hair restyling performance for several days without leaving the hair feeling unduly sticky or stiff, and without reapplication of the compositions described herein and/or application of additional styling aids on the hair.

Styling agents which are suitable for use in the present compositions comprise water-soluble polyalkylene glycols including, but not limited to, polyalkylene glycol homopolymers, polyethylene/polypropylene glycol copolymers, polyethylene/polypropylene diol copolymers, polyglycerins, and mixtures thereof, and/or their derivatives, and/or mixtures thereof. Within the scope of the present invention, the term "polyalkylene glycols" does not include polyalkylene glyceryl ethers. Additionally, in this context, "water-soluble" refers to those styling materials that have a solubility in water at 25° C. of greater than 0.6%, preferably greater than 1.0%, more preferably greater than about 1.5% by weight.

Preferred styling agents suitable for use herein include those water-soluble polyalkylene glycols of the formula:

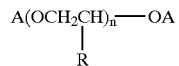

wherein each A is individually methyl or hydrogen, and wherein each R is individually hydrogen, methyl, or mixtures thereof. When R is hydrogen, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes and polypropylene glycols. When R is methyl, it is also understood that various positional isomers of the resulting polymers can exist.

In the above structure, n has an average value of from 4 to about 18, more preferably from about 6 to about 12, and even more preferably from about 8 to about 12.

In one embodiment, the polyalkylene glycol comprises a polyethylene glycol, a polypropylene glycol or an alkoxy polyethylene/polypropylene glycol copolymer. Specific examples of suitable polyalkylene glycol polymers include: polyethylene/polypropylene glycol copolymers (e.g., methoxy, ethoxy, propoxy, butoxy, and pentoxy polyethylene/polypropylene glycols), triglycerin, hexaglycerin, PPG-4, PPG-6, PEG-5, PEG-6, PEG-8, PEG-12, PEG-14, PEG-18, and mixtures thereof. Preferred in some embodiments are those polyalkylene glycols which have a number average molecular weight of from about 200 to about 900, specifically from about 300 to about 600, more specifically from about 400 to about 600, and having from about 4 to about 18, specifically from about 6 to about 12, more specifically from about 8 to about 12, repeating alkylene oxide radicals wherein each of the repeating alkylene oxide radicals has from 2 to 6 carbon atoms. Specific examples of the preferred polyalkylene glycols include, but are not limited to, PPG-4, wherein R equals methyl and n has an average value of about 4; PEG-8, wherein R equals H and n has an average value of about 8 (PEG-8 is available as Carbowax 400 from Union Carbide); PEG-12, wherein R equals H and n has an average value of about 12 (PEG-12 is available as Carbowax 600 from Union Carbide); and PEG-18, wherein R equals H and n has an average value of about 18 (PEG-18 is available as Carbowax 900 from Union Carbide).

In one embodiment, the compositions are substantially free of polyalkylene glycerol ethers. The term "substantially free" as used herein, unless otherwise specified, refers to preferred negative limitations of some embodiments of the compositions of the present invention, and are particularly directed to the amount and concentration of polyalkylene glyceryl ether styling agents, or derivatives thereof, in the compositions. The terms "substantially free" means that the compositions preferably contain less than an effective amount of such agents when used alone to provide any hair styling performance when the compositions are applied to the hair. In this context, the negative limitations pertain only to those polyalkylene glyceryl ether styling agents which are also a liquid or semi-solid under ambient conditions, and to compositions which do not contain silicone-containing materials. In further embodiments, the compositions preferably contain less than about 5%, more preferably, less than about 2%, even more preferably, less than about 1%, most preferably 0%, of such agents by weight of the compositions.

The hair care compositions typically comprise the styling agent in an amount which provides the desired styling properties. In one embodiment, the hair care compositions comprise the polyalkylene glycol styling agent in an amount of from about 5% to about 20%, more specifically in an amount of from about 5% to about 12%, even more specifically in an amount of from about 7% to about 10%, based on the weight of the composition.

Film Forming Polymer

In addition to the polyalkylene glycol styling agents, the hair care compositions of the present invention comprise film forming polymers that are soluble in the polyalkylene glycol styling agents. It is believed that the film forming polymer provides for increased styling strength delivered by the polyalkylene glycol styling agents of the present invention.

Preferred in some embodiments are those film forming polymers which have a molecular weight of greater than about 10,000, preferably greater than about 40,000. As the molecular weight of the film forming polymers increases, there may be a tendency for the film forming polymer to render hair treated with the hair care composition of the present invention undesirable. Accordingly, the molecular weight of the film forming polymer should be limited, if necessary to avoid this tendency. Film forming polymers which are suitable for use in the present compositions are soluble in the polyalkylene styling agents and include, but are not limited to, polyvinylpyrrolidone polymers and copolymers such as polyvinylpyrrolidone/vinyl acetate copolymers, polyvinylpyrrolidone/polyvinylcaprolactam copolymers, polyvinylpyrrolidone/dialkylaminoalkyl(meth) acrylamide copolymers, and polyvinylpyrrolidone/ polyvinylcaprolactam/dialkylaminoalkyl(meth)acrylamide terpolymers, polyvinylpyrrolidone/ dialkylaminoalkylacrylate copolymers, polyvinylpyrrolidone/polyvinylcaprolactam/ dialkylaminoalkyl(meth)acrylate terpolymers, hydrophilic polyurethanes, polyvinylcaprolactam polymers and copolymers, vinylacetate/crotonate/vinylneodecanoate terpolymers, isobutylene ethylmaleimide/ hydroxyethylmaleimide copolymers, octylacrylamide/ (meth)acrylate/alkylaminoalkyl(meth)acrylate terpolymers, and mixtures thereof, and/or their derivatives, and/or mixtures thereof.

Specific examples of preferred film forming polymers include, but are not limited to, polyvinylpyrrolidone/ vinylacetate (commercially available as Luviskol VA 73W from BASF), polyurethane-1 (commercially available as Luviset PUR from BASF or PUR 28-001A from National Starch), polyvinylcaprolactam (commercially available as Luvitec VCAP from BASF), polyvinylpyrrolidone/ polyvinylcaprolactam (commercially available as Luvitec VPC from BASF), polyvinylpyrrolidone/ dimethylaminopropylmethacrylamide (commercially available as Styleze CC-10 from ISP), polyvinylpyrrolidone/ polyvinylcaprolactam/ dimethylaminopropylmethacrylamide (commercially available as Aquaflex SF-40 from ISP), isobutylene ethylmaleimide/hydroxyethylmaleimide (commercially available as Aquaflex FX-64 from ISP), polyvinylpyrrolidone/dimethylaminoethylmethacrylate (commercially available as Copolymer 845 from ISP), quaternized polyvinylpyrrolidone/ dimethylaminoethylmethacrylate (commercially available as Gafquat 734, Gafquat 755, or Gafquat 755N from ISP), polyvinylpyrrolidone/polyvinylcaprolactam/ dimethylaminoethylmethacrylate (commercially available as Gaffix VC-713 from ISP), poly (vinylacetate/crotonates/ vinylneodecanoate) (commercially available as Resyn 28-2930 from National Starch), and octylacrylamide/ acrylate/butylaminoethylmethacrylate (commercially available as Amphomer from National Starch).

The hair care compositions typically comprise the film forming polymer in an amount suitable to increase the styling strength delivered by the polyalkylene styling agents of the present invention. In one embodiment, the hair care compositions comprise from about 0.1% to about 3%, more specifically from about 0.25% to about 1.5%, even more specifically from about 0.25% to about 0.75% of the film forming polymer, based on the weight of the composition.

The weight ratio of polyalkylene glycol styling agent to film forming polymer in the hair care compositions of the present invention ranges from about 5:1 to about 50:1, more specifically from about 10:1 to about 40:1, even more specifically from about 20:1 to about 40:1. If the ratio of polyalkylene glycol styling agent to film forming polymer is less than 5:1, hair treated with the hair care composition may feel sticky and the feel of the hair may become undesirable.

Liquid Carrier

The hair care compositions of the present invention also comprise any known or otherwise effective liquid carrier that is suitable for use in formulations intended for topical applications to human hair. The liquid carrier helps to solubilize or disperse the styling agents described hereinbefore. The liquid carrier may comprise one or more liquid carriers provided that the selected styling agent is sufficiently miscible or dispersible in the selected liquid carrier.

Suitable liquid carriers for use in the hair care compositions of the present invention include volatile liquid carrier materials. In this context, "volatile liquid carrier" refers to materials which have a boiling point of less than about 260°

C., preferably from about 50° C. to about 260° C., more preferably from about 60° C. to about 200° C. (at about one atmosphere of pressure). Nonlimiting examples of volatile liquid carriers include water, organic solvents such as $C_1$–$C_6$ alkanols, mono- and dialkyl ethers of diethylene (commercially available as Carbitol), and combinations thereof. Specific examples of suitable $C_1$–$C_6$ alkanols include, but are not limited to, ethanol, n-propanol, isopropanol, n-butanol, amyl alcohol and mixtures thereof. Preferred $C_1$–$C_6$ alkanols include $C_2$–$C_4$ monohydric alcohols such as ethanol, isopropanol and mixtures thereof. In one embodiment, the liquid carrier comprises water. In another embodiment, the liquid carrier comprises at least 50% water. In another embodiment, the liquid carrier comprises at least 75% water, more preferably at least 85% water. In yet another embodiment, the liquid carrier consists essentially of water.

The total concentration of the liquid carrier in the compositions of the present invention will vary with the type of liquid carrier selected, the type of styling agent used in combination with the liquid carrier, and the solubility of the selected styling agent in the selected liquid carrier. Preferred total concentration of the liquid carrier ranges from about 50% to about 95%, more preferably from about 85% to about 95%, and even more preferably from about 87% to about 93%, based on the weight of the composition.

The hair care compositions of the present invention provide hair care compositions which exhibit good wet and/or dry hair restyling performance and good hair look and feel for extended periods of time without the need to reapply the compositions or to apply any other styling aids. The hair care compositions of the present invention also provide leave-on hair styling compositions which do not feel unduly sticky or stiff after the composition has been applied and allowed to dry. Additionally, the hair care compositions of the present invention exhibit good styling aesthetics, including frizz and volume control, superior hold, and superior hair look and feel.

Optional Components

In addition to the components described above, the hair care compositions of the present invention may further comprise one or more optional components known or otherwise effective for use in hair care products, provided that the optional components are physically and chemically compatible with the components described above, or do not otherwise unduly impair product stability, aesthetics or performance. Nonlimiting examples of such optional components are disclosed in *International Cosmetic Ingredient Dictionary*, Fifth Edition, 1993, and *CTFA Cosmetic Ingredient Handbook*, Second Edition, 1992, both of which are incorporated by reference herein in their entirety.

Non-Volatile Silicone

For example, the hair care compositions of the present invention may further comprise one or more non-volatile silicones. When present, the silicone is typically present in the composition herein in an amount sufficient to provide desirable dry hair feel and softness. In one embodiment, the silicone may be included at a level of from about 0.25% to about 10%, specifically from about 1.0% to about 5%, more specifically from about 1% to about 3%, by weight of the hair care compositions.

Preferred in some embodiments are those silicones which have a number average molecular weight of greater than about 40,000, specifically greater than about 60,000, more specifically greater than about 80,000. In other embodiments, the silicone may have a molecular weight in excess of about 200,000.

The silicone may be added to the composition in any form. For example, it may be added to a propellant (in the case of aerosol products) or it may be added to the product as a neat fluid or as a pre-formed emulsion. When the silicone is added to the composition as a pre-formed surfactant-containing emulsion, the surfactant content (weight percent) in the emulsion should not exceed 25% of the silicone content of the emulsion or an undesirable hair feel could result. Because polymerization emulsions tend to require relatively high surfactant amounts in order to form the emulsion, it is preferred that if pre-formed emulsions are used that they be mechanical emulsions.

In one embodiment, the non-volatile silicone may be present in a volatile carrier or solvent, such as volatile silicones, branched chain hydrocarbons or mixtures thereof. Preferred silicones useful as the volatile carrier or solvent include cyclopentasiloxane (commercially available from General Electric Co. as SF1202), hexymethicone (commercially available from Archimica as Silcare 41M10), caprylil methicone (commercially available from Archimica as Silcare 41M15) and mixtures thereof.

Non-limiting examples of suitable nonvolatile silicones include nonvolatile soluble silicones, nonvolatile insoluble silicones, or combinations thereof. In this context, the term "soluble silicone" means that the silicone is miscible with the liquid carrier so as to form part of the same phase. Conversely, the term "insoluble silicone" means that the silicone forms a separate, discontinuous phase from the liquid carrier, such as in the form of an emulsion, microemulsion, or a suspension of droplets of the silicone. The term "nonvolatile silicone" as used in this context means that the silicone has a boiling point of at least about 265° C., preferably at least about 275° C., more specifically at least about 300° C. Such materials exhibit very low or no significant vapor pressure at ambient conditions.

Suitable nonvolatile insoluble silicones include those insoluble silicone fluids such as polyalkylsiloxanes, polyarylsiloxanes, polyalkylaryl siloxanes, polyether siloxane copolymers, and mixtures thereof. Other nonvolatile insoluble silicone fluids having feel enhancing properties can also be used.

Nonlimiting examples of silicone fluids for use in the hair styling compositions of the present invention include polyalkyl or polyaryl siloxanes which conform to the formula:

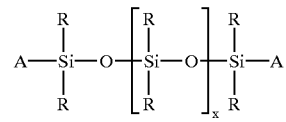

wherein R is alkyl or aryl, and x is an integer from about 7 to about 8,000. "A" represents groups which block the ends of the silicone chains.

The alkyl or aryl groups substituted on the siloxane chain (R) or at the ends of the siloxane chains (A) may have any structure as long as the resulting silicones remain fluid at ambient conditions, are hydrophobic, are neither irritating, toxic nor otherwise harmful when applied to the hair or skin, are compatible with the other components of the composition, are chemically stable under normal use and storage conditions, and are capable of being deposited on and improving the feel of hair.

Suitable A groups include methyl, ethyl, phenyl, phenylene, hydroxy, methoxy, ethoxy, propoxy, and aryloxy. The two R groups on the silicone atom may represent the same group or different groups. Preferably, the two R groups represent the same group. Suitable R groups include methyl, ethyl, propyl, phenyl, phenethyl, methylphenyl and phenylmethyl. The preferred silicone fluids are polydimethylsiloxane, polydiethylsiloxane, and polymethylphenylsiloxane. Polydimethylsiloxane is most preferred.

Specific examples of preferred nonvolatile insoluble silicone fluids include, but are not limited to, polydimethylsiloxanes such as the Viscasil R® and SF96® series (commercially available from the General Electric Co.), and the Dow Corning 200® series (commercially available from Dow Coming Corp.); polymethylphenylsiloxane such as SF1075® (commercially available from the General Electric Co.).

Pre-emulsified silicones are especially useful as they can usually be directly added to batch compositions without high shear mixing equipment. Examples of preferred silicone emulsions are SM2169 and SM2140 (commercially available from General Electric), DC1664 (commercially available from Dow Corning), BY22-029 (commercially available from Toray), and KM902 (commercially available from Shin-Etsu).

Other suitable silicone fluids are disclosed in U.S. Pat. No. 2,826,551, issued. to Green; U.S. Pat. No. 3,964,500, issued to Drakoff, U.S. Pat. No. 4,364,837, issued to Pader; and British Patent 849,433, issued to Woolston, all of which disclosures are incorporated herein by reference.

Other suitable silicones include insoluble silicone gum. The term "silicone gum", as used herein, means polyorganosiloxane materials having a viscosity at 25° C. of greater than or equal to 1,000,000 centistokes. Silicone gums are described by U.S. Pat. No. 4,152,416, Spitzer et al., issued May 1, 1979; and *Chemistry and Technology of Silicones*, New York: Academic Press 1968. The "silicone gums" will typically have a mass molecular weight in excess of about 200,000, generally between about 200,000 and about 1,000,000. Specific examples of preferred silicone gums include polydimethylsiloxane, (polydimethylsiloxane) (methylvinylsiloxane)copolymer, poly(dimethylsiloxane) (diphenylsiloxane)(methylvinylsiloxane)copolymer, and mixtures thereof.

Other suitable silicones include silicone resins. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be referred to as silicone resins herein. Preferably, the ratio of oxygen:silicon atoms is at least 1.2:1.0. Silanes used in the manufacture of silicone resins include monomethyl-, dimethyl-, trimethyl-, monophenyl-, diphenyl-methylphenyl-, monovinyl-, methylvinyl-chlorosilanes, and tetrachlorosilane, with the methyl-substituted silanes being most commonly utilized. Preferred resins are offered by General Electric as GE SS4230® and SS4267®. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in *Encyclopedia of Polymer Science and Engineering*, Volume 15, Second Edition, pp.204–308, John Wiley & Sons, Inc., 1989, incorporated herein by reference.

Propellant

The hair care compositions of the present invention may optionally further comprise one or more propellants suitable for aerosol delivery of the composition to the desired application surface. The total concentration of propellant, if included, in the aerosol hair care compositions typically ranges from about 5% to about 40%, specifically from about 5% to about 25%, more specifically from about 5% to about 15%, by weight of the composition.

Nonlimiting examples of suitable propellants include hydrocarbons, nitrogen, carbon dioxide, nitrous oxide, atmospheric gas, 1,2-difluoroethane (Hydrofluorocarbon 152A) supplied as Dymel 152A by Dupont, dimethylether, and mixtures thereof. Preferred are the hydrocarbon propellants, specific examples of which include propane, butane, and isobutane. Most preferred is a hydrocarbon containing a mixture of propane and isobutane, specific examples of which include Aeron A-46 and Aeron A-70 (both are commercially available from Diversified CPC).

In one embodiment, the aerosol hair care compositions of the present invention can be contained or dispensed in any known or otherwise effective aerosol container or delivery system. All such containers or delivery systems should be compatible with the ingredients of the hair care compositions of the present invention. Alternatively, pressurized aerosol dispensers can be used where the propellant is separated from contact with the hair care composition by use of specialized containers such as a two compartment can of the type sold under the tradename SEPRO from American National Can Corp.

Gelling Agent/Thickener

The hair care compositions of the present invention preferably further comprise a gelling agent to help provide the desired viscosity to the residue which remains on the hair after the composition has been applied and allowed to dry on the hair. The preferred optional gelling agent also helps to provide for improved hair hold performance. Suitable optional gelling agents include any material known or otherwise effective in providing any gelling or measurable viscosity increase to the residue. The concentration of the optional gelling agent in the compositions typically ranges from about 0.1% to about 10%, preferably from about 0.2% to about 5.0%, by weight of the compositions.

Nonlimiting examples of suitable optional gelling agents include crosslinked carboxylic acid polymers; unneutralized crosslinked carboxylic acid polymers; unneutralized modified crosslinked carboxylic acid polymers; crosslinked ethylene/maleic anhydride copolymers; unneutralized crosslinked ethylene/maleic anhydride copolymers (e.g., EMA 81 commercially available from Monsanto); unneutralized crosslinked allyl ether/acrylate copolymers (e.g., Salcare SC90 commercially available from Allied Colloids); unneutralized crosslinked copolymers of sodium polyacrylate, mineral oil, and PPG-1 trideceth-6 (e.g., Salcare SC91 commercially available from Allied Colloids); unneutralized crosslinked copolymers of methyl vinyl ether and maleic anhydride (e.g., Stabileze QM-PVMIMA copolymer commercially available from International Speciality Products); hydrophobically modified nonionic cellulose polymers; hydrophobically modified nonionic cellulose polymers; hydrophobically modified ethoxylate urethane polymers (e.g., Ucare Polyphobe Series of alkali swellable polymers commercially available from Union Carbide); and combinations thereof. In this context, the term "unneutralized" means that the optional polymer and copolymer gelling agent materials contain unneutralized acid monomers.

Preferred optional gelling agents include water-soluble unneutralized crosslinked ethylene/maleic anhydride copolymers, water-soluble unneutralized crosslinked carboxylic acid polymers, and water-soluble hydrophobically modified nonionic cellulose polymers. The crosslinked carboxylic acid polymers and hydrophobically modified nonionic cellulose polymers are described in detail hereinbelow.

The optional carboxylic acid polymers suitable for use herein include those crosslinked compounds containing one or more monomers derived from acrylic acid, substituted acrylic acids, esters of acrylic acid, esters of substituted acrylic acids, corresponding salts thereof, and combinations thereof, wherein the crosslinking agent contains two or more carbon-carbon double bonds and is derived from a polyhydric alcohol. Specific examples of these carboxylic acid polymers include crosslinked carboxylic acid homopolymers and crosslinked carboxylic acid copolymers. Combinations of these two types of polymers are also useful herein.

The term "substituted" as used herein refers to chemical moieties known or otherwise effective for attachment to gelling agents or other compounds. Such substituents include those listed and described in C. Hansch and A. Leo, *Substituent Constants for Correlation Analysis in Chemistry and Biology* (1979), which listing and description are incorporated herein by reference. Examples of such substituents include, but are not limited to, alkyl, alkenyl, alkoxy, hydroxy, oxo, nitro, amino, aminoalkyl (e.g., aminomethyl, etc.), cyano, halo, carboxy, alkoxyacyl (e.g., carboethoxy, etc.), thiol, aryl, cycloalkyl, heteroaryl, heterocycloalkyl (e.g., piperidinyl, morpholinyl, pyrrolidinyl, etc.) imino, thioxo, hydroxyalkyl, aryloxy, arylalkyl, and combinations thereof.

The term "corresponding salts" as used herein refers to cationic salts formed at any acidic (e.g., carboxyl) group, or anionic salts formed at any basic (e.g., amino) group, either of which are suitable for topical application to human skin. Many such salts are known in the art, examples of which are described in World Patent Publication WO 87/05297, Johnston et al., published Sep. 11, 1987, which description is incorporated herein by reference.

Preferred optional crosslinked carboxylic acid polymers include those crosslinked carboxylic acid homopolymers or copolymers which contain unneutralized acid monomers. It has been found that crosslinked carboxylic acid polymers which have unneutralized acid monomers are especially effective in providing gelling properties to the residue without suppressing the ease of removability of the residue by shampooing the hair.

Partially or fully neutralized crosslinked carboxylic acid polymers are also suitable for use as an optional gelling agent in the hair care compositions of the present invention, provided that these carboxylic acid polymers are included in combination with one or more styling agents which have an average solubility parameter of above about 14 $(cal/cm^3)^{0.5}$ to about 20 $(cal/cm^3)^{0.5}$. Solubility parameters for the styling agents or other materials, and means for determining such parameters, are well known in the chemical arts. A description of solubility parameters and means for determining them are described by C. D. Vaughan, "Solubility Effects in Product, Package, Penetration and Preservation" 103 *Cosmetics and Toiletries* 47–69, October 1988; and C. D. Vaughn, "Using Solubility Parameters in Cosmetics Formulation", 36 *J. Soc. Cosmetic Chemists* 319–333, September/October, 1988, which descriptions are incorporated herein by reference.

Suitable crosslinked carboxylic acid homopolymers include those crosslinked copolymers which have a first monomer selected from the group consisting of an acrylic acid or derivative thereof as defined above, a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e., $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Preferred first monomers include acrylic acid, methacrylic acid, and ethacrylic acid, $C_{1-4}$ alcohol acrylate esters, $C_{1-4}$ alcohol methyacrylate esters, $C_{1-4}$ alcohol ethacrylate esters, and mixtures thereof, with acrylic acid, methacrylic acid, $C_{1-4}$ alcohol acrylate esters, $C_{1-4}$ alcohol methacrylate esters, and mixtures thereof being the most preferred. Preferred second monomers include $C_{8-40}$ alkyl acrylate esters, with $C_{10-30}$ alkyl acrylate esters being the most preferred. In other words, the preferred crosslinked carboxylic acid copolymers include those copolymers which have a first monomer selected from the group consisting of acrylic acid, methacrylic acid, $C_{1-4}$ alcohol acrylate esters, $C_{1-4}$ alcohol methacrylate esters, and mixtures thereof, and a $C_{10-30}$ alkyl acrylate ester second monomer.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinking agents are those selected from the group consisting of allyl ethers of sucrose, allyl ethers of pentaerythritol, and mixtures thereof.

Examples of commercially available crosslinked carboxylic acid homopolymers suitable for use herein include the carbomers, which are homopolymers of acrylic acid crosslinked with allyl ethers of sucrose or pentaerytritol. The carbomers are available as the Carbopol® 900 series from B.F. Goodrich. Most preferred are the commercially available carbomers which have unneutralized acid monomers.

Examples of commercially available crosslinked carboxylic acid copolymers suitable for use herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Pemulen TR-1, and Pemulen TR-2, from B.F. Goodrich.

Suitable crosslinked carboxylic acid polymers are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which descriptions are incorporated by reference herein. See also, *CTFA International Cosmetic Ingredient Dictionary*, fourth edition, 1991, pp. 12 and 80; which description is also incorporated herein by reference.

The preferred optional gelling agents suitable for use in the hair care compositions of the present invention also include water-soluble hydrophobically modified nonionic cellulose polymers. The term "water-soluble hydrophobically modified nonionic polymers" refers to those water-soluble nonionic polymers which have been modified to comprise substituted hydrophobic groups to make the polymer less soluble in water. Hence, the nonionic cellulose polymers comprise a water-soluble cellulosic chain (or hydrophilic cellulosic chain) which forms the backbone, wherein the backbone comprise substituted hydrophobic groups. Suitable substituted hydrophobic groups include $C_8$–$C_{22}$ alkyl, arylalkyl, alkylaryl groups, and mixtures thereof. The degree of substitution on the backbone should be from about 0.10% to about 1.0%, depending on the particular polymer backbone. The nonionic cellulose polymers generally contain a ratio of hydrophilic substituents to hydrophobic substituents of from about 10:1 to about 1000:1.

Nonlimiting examples of preferred hydrophobically modified nonionic cellulose polymers include those nonionic cellulose polymers which comprise a cellulose ether substrate and a long chain alkyl modifier. In this context, the term "long chain alkyl modifier" means that the modifying compound can comprise an alkyl radical or other functional groups such as an alphahydroxyalkyl radical, a urethane radical, or an acyl radical. These polymers, and methods of making the polymers, are also described in U.S. Pat. No. 4,228,277, issued to Landoll on Oct. 14, 1980, which description is incorporated herein by reference.

Suitable cellulose ether substrates include any known or otherwise effective water-soluble nonionic cellulose ether. Nonlimiting examples of suitable water-soluble nonionic cellulose ethers include, but are not limited to, the hydroxyethyl cellulose, hydroxypropyl cellulose, methyl cellulose, hydroxypropyl methyl cellulose, ethyl hydroxyethyl cellulose, and methyl hydroxyethyl cellulose. The amount of the nonionic substituent (e.g., methyl, hydroxyethyl, or hydroxypropyl substituent) is not critical provided that the amount is sufficient to assure that the ether is water-soluble.

The preferred cellulose ether substrate is hydroxyethyl cellulose (HEC) which has a weight average molecular weight from about 50,000 to about 700,000. It has been found that hydroxyethyl cellulose is the most hydrophilic suitable cellulose ether substrate, and therefore, can allow for greater modification than other suitable water-soluble cellulose ether substrates before water-insolubility is achieved. Accordingly, control of the modification process and control of the properties of the modified substrate can be more precise with hydroxyethyl cellulose substrates. Hydrophilicity of the most commonly used nonionic cellulose ethers ranges from hydroxyethyl to hydroxypropyl to hydroxypropylmethyl to methyl, with hydroxyethyl being the most hydrophilic and methyl being the least hydrophilic.

The long chain alkyl modifier can be attached to the cellulose ether substrate via an ether, ester, or urethane linkage. The ether linkage is preferred. The size and effect of the hydrocarbon chain of suitable modifiers effectively conceals any noticeable effect derived from functional groups other than alkyl halides which links the modifier to the substrate. In other words, if the long chain alkyl modifier is an epoxide containing an alphahydroxyalkyl radical, an isocyanate containing a urethane radical, or an acyl chloride containing an acyl radical, the effect of these functional groups are unnoticeable and the performance of the hydrophobically modified nonionic cellulose polymer is not significantly different from a polymer modified with an alkyl halide modifier.

Specific examples of preferred hydrophobically modified nonionic cellulose polymers include Natrosol Plus Grade 330, and Natrosol Plus CS Grade D-67, both commercially available from the Aqualone Company located in Wilmington, Del. Natrosol Plus Grade 330 is a hydrophobically modified hydroxyethylcellulose which has a weight average molecular weight of approximately 300,000 prior to modification; which has been submitted with from about 0.4% to about 0.8%, by weight, of an alkyl modifier having sixteen carbon atoms; and which has a hydroxyethyl molar substitution of from about 3.0 to about 3.7. Natrosol Plus CS Grade D-67 is a hydrophobically modified hydroxyethylcellulose which has a weight average molecular weight of approximately 700,000 prior to modification; which has been substituted with from about 0.50% to about 0.95%, by weight, of an alkyl modifier having sixteen carbon atoms; and which has a hydroxyethyl molar substitution of from about 2.3 to about 3.3.

Other cellulose polymers which can provide measurable viscosity increase to the residue are also suitable for use as an optional gelling agent herein. A specific example of other suitable cellulose polymers includes a water-soluble hydrophobically modified cationic cellulose polymer commercially available as Quatrosoft from Amerchol.

Additional Optional Materials

Other optional materials suitable for use in the hair care compositions of the present invention include, but are not limited to, preservatives, surfactants, conditioning polymers, electrolytes, fatty alcohols, hair dyes, anti-dandruff actives, odor masking agents, pH adjusting agents, perfume oils, perfume solubilizing agents, sequestering agents, emollients, lubricants and penetrates such as various lanolin compounds and protein hydrolysates. The concentration of such optional ingredients generally ranges from zero to about 25%, more typically from about 0.05% to about 15%, even more typically from about 0.1% to about 10%, by weight of the composition.

The hair care compositions of the present invention are used in conventional ways, including as mousses, gels, lotions, pumps and hair sprays, to provide hairstyle/hold benefits without having to reapply the compositions for several days. An effective amount of the composition is either sprayed or applied onto wert and/or dry hair before or after the hair is styled. As used herein, "effective amount" means an amount sufficient to provide the hair hold and style performance desired according to the length and texture of the hair. Typically, the composition is applied to hair in need of such treatment.

The following examples further illustrate various embodiments within the scope of the present invention. The examples are given solely for the purposes of illustration and are not to be construed as limitations of the present invention, as many variations of the invention are possible without departing from the spirit and scope of the invention. In the examples and throughout the present specification, parts and percentages are by weight unless otherwise indicated. Ingredients are identified by chemical or CFTA name. In the following tables, all such weight percentages, as they pertain to listed ingredients, are based on the commercial products employed, and in the case of commercial products which are not in neat form, the active level is shown in parentheses by weight percent of the composition.

EXAMPLES I–X

The following Examples I–X are hair cream compositions representative of the present invention. Each of the compositions defined by Examples I–X is prepared by by combining all of the listed premix ingredients while maintaining adequate mixing and heating to approximately 50° C. Incorporation of each of the premix ingredients should be complete before proceeding to the next addition. The combination is then cooled to ambient temperature. Next, the thickeners and neutralizers are added to the premix ingredients while maintaining adequate mixing. Each of the exemplified hair cream compositions provides improved hair restyle performance without the need to reapply the composition or to apply any other additional styling aids.

TABLE I

Hair Cream Compositions

| Component, wt. % | I | II | III | IV | V |
|---|---|---|---|---|---|
| PREMIX | | | | | |
| Water | 82.03 | 78.03 | 75.58 | 76.78 | 74.75 |
| Film Forming Polymer (% active) | | | | | |
| PVP/VA (1) | 1.0 (0.5) | 2.0 (1.0) | — | 1.0 (0.5) | 1.0 (0.5) |
| Polyurethane-1 (2) | — | — | 3.0 (0.9) | — | — |
| Polyvinylcaprolactam (3) | — | — | — | 3.0 (0.9) | — |
| Styling Agent | | | | | |
| PEG-8 (4) | — | — | — | 2.0 | 5.0 |
| PEG-12 (5) | 10.0 | 10.0 | 12.0 | 10.0 | 10.0 |
| Hexymethicone (6) | — | — | 5.0 | — | — |
| Caprylil Methicone (7) | — | — | — | 2.5 | — |
| Cyclopentasiloxane (8) | 2.0 | 2.0 | — | 2.5 | 5.0 |
| Silicone Emulsion (9) (% active) | — | 3.0 (1.5) | — | — | 2.0 (1.0) |
| Isosteareth-20 | 0.65 | 0.65 | 0.3 | — | 0.5 |
| Undeceth-9 | — | — | 0.3 | 0.4 | — |
| Benzyl Alcohol | 0.5 | 0.5 | 0.5 | 0.5 | 0.5 |
| Phenoxyethanol | 0.3 | 0.3 | 0.3 | 0.3 | 0.3 |
| Methyl Paraben | 0.2 | 0.2 | 0.2 | — | 0.2 |
| Disodium EDTA | 0.12 | 0.12 | 0.12 | 0.12 | 0.12 |
| Perfume | 0.2 | 0.2 | 0.2 | 0.1 | 0.1 |
| THICKENERS (% active) | | | | | |
| Salcare SC96 (10) | 3.0 (1.5) | 3.0 (1.5) | 2.5 (1.25) | — | — |
| Carbopol 934 (11) | — | — | — | 0.6 | 0.4 |
| NEUTRALIZER | | | | | |
| Aminomethylpropanol | — | — | — | 0.2 | 0.13 |

(1) Luviskol VA 73W (50% polyvinylpyrrolidone/vinyl acetate copolymer) from BASF
(2) Luviset PUR (30% polyurethane) from BASF
(3) Luvitec VCAP (30% poyvinylcaprolactam) from BASF
(4) Carbowax 400 from Union Carbide
(5) Carbowax 600 from Union Carbide
(6) Silcare 41M10 from Archimica
(7) Silcare 41M15 from Archemica
(8) SF1202 from GE
(9) 50% dimethicone emulsion from Toray Silicones
(10) 50% Polyquaternium 37 from Allied Colloids
(11) Crosslinked carboxylic acid homopolymer from BF Goodrich

TABLE II

Hair Cream Compositions

| Component, wt. % | VI | VII | VIII | IX | X |
|---|---|---|---|---|---|
| PREMIX | | | | | |
| Water | 70.93 | 84.03 | 78.53 | 75.68 | 78.18 |
| Film Forming Polymer (% active) | | | | | |
| PVP/VA (1) | 2.0 (1.0) | 1.0 (0.5) | 0.3 (0.15) | — | 1.0 (0.5) |
| PVP/dimethylaminopropyl methacrylamide (2) | — | — | 1.0 (0.1) | — | — |
| Polyvinylacetate/crotonate/vinylneodecanoate terpolymer(3) | — | — | — | 1.0 | 0.5 |
| Styling Agent | | | | | |
| PEG-8 (4) | 10.0 | — | — | 5.0 | — |
| PEG-12 (5) | 10.0 | 10.0 | 12.0 | 10.0 | 10.0 |
| Hexymethicone (6) | — | — | 2.0 | — | — |
| Caprylil Methicone (7) | — | — | 2.0 | 2.5 | — |
| Cyclopentasiloxane (8) | — | 2.0 | — | 2.5 | 3.0 |

TABLE II-continued

Hair Cream Compositions

| Component, wt. % | VI | VII | VIII | IX | X |
|---|---|---|---|---|---|
| Silicone Emulsion (9) (% active) | 2.0 (1.0) | — | — | — | 2.0 (1.0) |
| Isosteareth-20 | 0.65 | 0.65 | 0.45 | — | 0.65 |
| Undeceth-9 | 0.15 | — | 0.2 | 0.4 | 0.15 |
| Benzyl Alcohol | 0.5 | 0.5 | 0.5 | 0.5 | 0.5 |
| Phenoxyethanol | 0.3 | 0.3 | — | 0.3 | 0.3 |
| Methyl Paraben | 0.2 | 0.2 | 0.2 | — | — |
| Disodium EDTA | 0.12 | 0.12 | 0.12 | 0.12 | 0.12 |
| TiO2 | — | 0.1 | — | — | — |
| Laponite XLG (10) | — | — | — | 1.0 | — |
| Perfume | 0.15 | 0.2 | 0.2 | 0.1 | 0.1 |
| THICKENERS (% active) | | | | | |
| Salcare SC96 (11) | 3.0 (1.5) | — | 2.5 (1.25) | — | 3.5 (1.75) |
| Permulan TR-1 (12) | — | 0.5 | — | 0.5 | — |
| NEUTRALIZER | | | | | |
| Triethanolamine | — | 0.4 | — | 0.4 | — |

(1) Luviskol VA 73W (50% polyvinylpyrrolidone/vinyl acetate copolymer) from BASF
(2) Styleze CC-10 (10% PVP/dimethylaminopropyl methacrylamide) from ISP
(3) Resyn 28-2930 for National Starch
(4) Carbowax 400 from Union Carbide
(5) Carbowax 600 from Union Carbide
(6) Silcare 41M10 from Archimica
(7) Silcare 41M15 from Archemica
(8) SF1202 from GE
(9) 50% dimethicone emulsion from Toray Silicones
(10) Clay from Southern Clay Products
(11) 50% Polyquaternium 37 from Allied Colloids
(12) Crosslinked carboxylic acid homopolymer from BF Goodrich

EXAMPLES XI–XV

The following Examples XI–XV are hair mousse compositions representative of the present invention. Each of the compositions defined by Examples XI–XV is prepared by combining all of the listed ingredients, except the propellant, and mixing the combination until all listed materials are dispersed in the batch while heating to approximately 50° C. The combination is then cooled to ambient temperature. The resultant liquid mixture is then filled into an aerosol container, and the propellant is added. Each of the exemplified hair mousse compositions provides improved hair restyle performance without the need to reapply the compositions or to apply any other additional styling aids.

TABLE III

Hair Mousse Compositions

| Component, wt. % | XI | XII | XIII | XIV | XV |
|---|---|---|---|---|---|
| Water | 77.48 | 72.63 | 73.28 | 70.08 | 72.08 |
| Film Forming Polymer (% active) | | | | | |
| PVP/VA (1) | 1.0 (0.5) | 2.0 (1.0) | 0.3 (0.15) | — | 1.0 (0.5) |
| PVP/dimethylaminopropyl methacrylamide (2) | — | — | 1.0 (0.1) | — | — |
| Polyvinylacetate/crotonate/vinylneodecanoate terpolymer (3) | — | — | — | 1.0 | 0.5 |
| Styling Agent | | | | | |
| PEG-8 (4) | — | — | — | 5.0 | — |
| PEG-12 (5) | 10.0 | 10.0 | 12.0 | 10.0 | 10.0 |
| Hexymethicone (6) | — | — | 2.0 | — | — |
| Caprylil Methicone (7) | — | — | — | 2.5 | — |
| Cyclopentasiloxane (8) | — | 2.0 | — | — | 3.0 |
| Silicone Emulsion (9) (% active) | — | 2.0 (1.0) | — | — | 2.0 (1.0) |
| Isosteareth-20 | — | 0.45 | 0.3 | — | 0.2 |
| Undeceth-9 | 0.3 | — | 0.2 | 0.4 | 0.2 |
| Benzyl Alcohol | 0.5 | 0.5 | 0.5 | 0.5 | 0.5 |
| Phenoxyethanol | 0.3 | — | — | 0.3 | 0.3 |
| Methyl Paraben | 0.2 | 0.2 | 0.2 | — | — |
| Disodium EDTA | 0.12 | 0.12 | 0.12 | 0.12 | 0.12 |
| Perfume | 0.1 | 0.1 | 0.1 | 0.1 | 0.1 |

TABLE III-continued

Hair Mousse Compositions

| Component, wt. % | XI | XII | XIII | XIV | XV |
|---|---|---|---|---|---|
| Propellant Aeron A-46 (10) | — | — | 10.0 | 5.0 | — |
| Propellant Aeron A-70 (10) | 10.0 | 10.0 | — | 5.0 | 10.0 |

(1) Luviskol VA 73W (50% polyvinylpyrrolidone/vinyl acetate copolymer) from BASF
(2) Styleze CC-10 (10% PVP/dimethylaminopropyl methacrylamide) from ISP
(3) Resyn 28-2930 from National Starch
(4) Carbowax 400 from Union Carbide
(5) Carbowax 600 from Union Carbide
(6) Silcare 41M10 from Archimica
(7) Silcare 41M15 from Archimica
(8) SF1202 from GE
(9) 50% dimethicone emulsion from Toray Silicones
(10) Propane/isobutane from Diversified CPC

EXAMPLES XVI–XVIII

The following Examples XVI–XVIII are spay-on gel compositions representative of the present invention. Each of the compositions defined by Examples XVI–XVIII is prepared by combining all of the listed ingredients, except the propellant, and mixing the combination until all listed materials are dispersed in the batch. The resultant composition is then filled into an aerosol container, and the propellant is added. Each of the exemplified spray-on gel compositions provides improved hair restyle performance without the need to reapply the compositions or to apply any other additional styling aids.

TABLE IV

Spray-on-gel Compositions

| Component, wt. % | XVI | XVII | XVIII |
|---|---|---|---|
| Water | 44.10 | 42.70 | 38.90 |
| Ethanol, Denatured | 10.0 | 10.0 | 15.0 |
| Film Forming Polymer (% active) | | | |
| PVP/VA (1) | 0.8 (0.4) | — | 1.0 (0.5) |
| Polyurethane-1 (2) | — | — | 1.0 (0.3) |
| Polyvinylcaprolactam (3) | — | 2.0 (0.6) | — |
| Styling Agent | | | |
| PEG-8 (4) | — | 5.0 | 12.0 |
| PEG-12 (5) | 8.0 | 5.0 | — |
| Hexymethicone (6) | 5.0 | — | — |
| Cyclopentasiloxane (7) | 2.0 | 2.0 | — |
| Silicone Emulsion (8) (% active) | — | 3.0 (1.5) | 2.0 (1.0) |
| Isosteareth-20 | — | 0.1 | — |
| Perfume | 0.1 | 0.2 | 0.1 |
| Isobutane | 5.0 | — | — |
| Dimethyl Ether | 25 | 30 | 30 |

(1) Luviskol VA 73W (50% polyvinylpyrrolidone/vinyl acetate copolymer) from BASF
(2) Luviset PUR (30% polyurethane) from BASF
(3) Luvitec VCAP (30% polyvinylcaprolactam) from BASF
(4) Carbowax 400 from Union Carbide
(5) Carbowax 600 from Union Carbide
(6) Silcare 41M10 from Archimica
(7) SF1202 from GE
(8) 50% dimethicone emulsion from Toray Silicones

EXAMPLES XIX–XXI

The following Examples XIX–XXI are pump hair spray compositions representative of the present invention. Each of the compositions defined by Examples XIX–XXI is prepared by combining all of the listed premix ingredients while maintaining adequate mixing and heating to approximately 50° C. Incorporation of each of the premix ingredients should be complete before proceeding to the next addition. The combination is then cooled to ambient temperature. Next, the thickeners and neutralizers are added to the premix ingredients while maintaining adequate mixing. Each of the exemplified hair spray compositions provides improved hair restyle performance without the need to reapply the composition or to apply any other additional styling aids.

TABLE V

Pump Hair Spray Compositions

| Component, wt. % | XIX | XX | XXI |
|---|---|---|---|
| PREMIX | | | |
| Water | 59.48 | 75.58 | 82.68 |
| Ethanol, Denatured | 10.0 | — | — |
| Film Forming Polymer (% active) | | | |
| PVP/VA (1) | 2.0 (1.0) | 1.0 (0.5) | 1.0 (0.5) |
| PVP/dimethylaminopropyl methacrylamide (2) | — | 4.0 (0.4) | — |
| Styling Agent | | | |
| PEG-8 (3) | 10.0 | — | — |
| PEG-12 (4) | 10.0 | 12.0 | 10.0 |
| Hexymethicone (5) | 5.0 | — | — |
| Caprylil Methicone (6) | — | 3.0 | — |
| Cyclopentasiloxane (7) | — | 2.0 | 3.0 |
| Silicone Emulsion (8) (% active) | 2.0 (1.0) | — | 2.0 (1.0) |
| Isosteareth-20 | 0.3 | 0.3 | 0.15 |
| Undeceth-9 | — | — | 0.15 |
| Benzyl Alcohol | 0.5 | 0.5 | 0.5 |
| Phenoxyethanol | 0.3 | 0.3 | 0.3 |
| Methyl Paraben | 0.2 | 0.2 | — |
| Disodium EDTA | 0.12 | 0.12 | 0.12 |
| Perfume | 0.1 | 0.1 | 0.1 |
| THICKENER | | | |
| Permulan TR-1 (9) | — | 0.5 | — |
| NEUTRALIZER | | | |
| Triethanolamine | — | 0.4 | — |

(1) Luviskol VA 73W (50% polyvinylpyrrolidone/vinyl acetate copolymer) from BASF
(2) Styleze CC-10 (10% PVP/dimethylaminopropyl methacrylamide) from ISP
(3) Carbowax 400 from Union Carbide
(4) Carbowax 600 from Union Carbide
(5) Silcare 41M10 from Archimica
(6) Silcare 41M15 from Archimica
(7) SF1202 from GE
(8) 50% dimethicone emulsion from Toray Silicones
(9) Crosslinked carboxylic acid homopolymer from BF Goodrich The specific embodiments and examples set forth above are provided for illustrative purposes only and are not intended to limit the scope of the following claims. Additional embodiments of the invention and advantages provided thereby will be apparent to one of ordinary skill in the art and are within the scope of the claims.

What is claimed is:

1. A hair care composition comprising:
   a) a water-soluble polyalkylene glycol having a average molecular weight of from about 200 to about 900 and from about 4 to about 18 repeating alkylene oxide radicals, wherein each of the repeating alkylene oxide radicals has from 2 to 6 carbon atoms;
   b) a film forming polymer, wherein the film forming polymer is soluble in the polyalkylene glycol and wherein the weight ratio of the polyalkylene glycol to the film forming polymer ranges from about 5:1 to about 50:1; and
   c) a liquid carrier wherein the liquid carrier is selected from the group consisting of water, $C_1$–$C_6$ alkanols, mono- or dialkyl ethers of diethylene glycol, or mixtures thereof.

2. A method for styling hair, which method comprises applying the composition of claim 1 to hair.

3. A hair care composition comprising:
   a) from about 5% to about 20%, by weight of the composition, of a water-soluble polyalkylene glycol having a average molecular weight of from about 200 to about 900 and from about 4 to about 18 repeating alkylene oxide radicals, wherein each of the repeating alkylene oxide radicals has from 2 to 6 carbon atoms;
   b) a film forming polymer, wherein the film forming polymer is soluble in the polyalkylene glycol and wherein the weight ratio of the polyalkylene glycol to the film forming polymer ranges from about 5:1 to about 50:1; and
   c) a liquid carrier selected from the group consisting of water, $C_1$–$C_6$ alkanols, mono- or dialkyl ethers of diethylene glycol, or mixtures thereof.

4. The composition of claim 3, wherein the composition comprises:
   a) from about 5% to about 12%, by weight of the composition, of the water-soluble polyalkylene glycol;
   b) from about 0.1% to about 3%, by weight of the composition, of the film forming polymer; and
   c) from about 50% to about 95%, by weight of the composition, of the liquid carrier.

5. The composition of claim 3, wherein the composition comprises from about 7% to about 10%, by weight of the composition, of the water-soluble polyalkylene glycol.

6. The composition of claim 3, wherein the film forming polymer comprises polyvinylpyrrolidone polymer or copolymer, hydrophilic polyurethane, polyvinylcaprolactam polymer or copolymer, isobutylene ethylmaleimide/hydroxyethylmaleimide copolymer, vinylacetate/crotonate/vinylneodecanoate terpolymer, octylacrylamide/acrylate/alkylaminoalkylacrylate terpolymer, or a mixture thereof.

7. The composition of claim 6, wherein the film forming polymer is selected from the group consisting of polyvinylpyrrolidone, polyvinylpyrrolidone/vinyl acetate, polyurethane-1, polyvinylcaprolactam, polyvinylpyrrolidone/polyvinylcaprolactam, polyvinylpyrrolidone/dimethylaminopropylmethacrylamide, polyvinylpyrrolidone/polyvinylcaprolactam/dimethylaminopropylmethacrylamide, isobutylene ethylmaleimide/hydroxyethylmaleimide, polyvinylpyrrolidone/dimethylaminoethylmethacrylate, polyvinylpyrrolidone/polyvinylcaprolactam/dimethylaminoethylmethacrylate, octylacrylamide/acrylate/butylaminoethylmethacrylate, polyvinylacetate/crotonate/vinylneodecanoate and mixtures thereof.

8. The composition of claim 3, wherein the weight ratio of the polyalkylene glycol to the film forming polymer ranges from about 10:1 to about 40:1.

9. The composition of claim 3, wherein the composition comprises from about 85% to about 95% by weight of the composition, of the liquid carrier.

10. The composition of claim 3, wherein the composition further comprises a propellant.

11. The composition of claim 3, wherein the composition further comprises a gelling agent, and wherein the gelling agent is a water-soluble polymer comprising crosslinked ethylene/maleic anhydride copolymer, crosslinked carboxylic acid polymer, hydrophobically-modified nonionic cellulose polymer, or mixtures thereof.

12. The composition of claim 3, wherein the composition further comprises a non-volatile silicone with a molecular weight greater than about 40,000 daltons.

13. A method for styling hair, which method comprises applying the composition of claim 3 to hair.

14. The composition of claim 3, wherein the water-soluble polyalkylene glycol comprises polyethylene glycol, polypropylene glycol or alkoxy polyethylene/polypropylene glycol copolymer.

15. The composition of claim 14, wherein the water soluble polyalkylene glycol is selected from the group consisting of ethoxy polyethylene/polypropylene glycol copolymers, methoxy polyethylene/polypropylene glycol copolymers, propoxy polyethylene/polypropylene glycol copolymers, butoxy polyethylene/polypropylene glycol copolymers, pentoxy polyethylene/polypropylene glycol copolymers, triglycerin, hexglycerin, PPG-4, PPG-6, PEG-5, PEG-6, PEG-8, PEG-12, PEG-14, PEG-18, and mixtures thereof.

16. The composition of claim 3, wherein the composition comprises from about 0.25% to about 1.5% by weight of the composition, of the film forming polymer.

17. The composition of claim 16, wherein the composition comprises from about 0.25% to about 0.75% by weight of the composition, of the film forming polymer.

18. A hair care composition comprising:
   a) from about 5% to about 12%, by weight of the composition, of a water-soluble polyalkylene glycol having a average molecular weight of from about 200 to about 900 and from about 4 to about 18 repeating alkylene oxide radicals, wherein each of the repeating alkylene oxide radicals has from 2 to 6 carbon atoms;
   b) from about 0.25% to about 1.5%, by weight of the composition, of a film forming polymer, wherein the film forming polymer is soluble in the polyalkylene glycol and wherein the weight ratio of the polyalkylene glycol to the film forming polymer ranges from about 10:1 to about 40:1; and
   c) from about 85% to about 95%, by weight, of a liquid carrier wherein the liquid carrier is selected from the group consisting of water, $C_1$–$C_6$ alkanols, mono- or dialkyl ethers of diethylene glycol, or mixtures thereof.

19. A hair care composition comprising:
   a) from about 5% to about 12%, by weight of the composition, of a water-soluble polyalkylene glycol having a average molecular weight of from about 200 to about 900 and from about 4 to about 18 repeating alkylene oxide radicals, wherein each of the repeating alkylene oxide radicals has from 2 to 6 carbon atoms;

b) from about 0.25% to about 1.5%, by weight of the composition, of a film forming polymer, wherein the film forming polymer is soluble in the polyalkylene glycol and wherein the weight ratio of the polyalkylene glycol to the film forming polymer ranges from about 10:1 to about 40:1;

c) from about 85% to about 95%, by weight of the composition, of a liquid carrier wherein the liquid carrier is selected from the group consisting of water, $C_1$–$C_6$ alkanols, mono- or dialkyl ethers of diethylene glycol, or mixtures thereof; and d) from about 1% to about 5%, by weight of the composition, of a non-volatile silicone with a molecular weight greater than about 40,000 daltons.

* * * * *